(12) United States Patent
Currie

(10) Patent No.: US 6,979,088 B2
(45) Date of Patent: Dec. 27, 2005

(54) MULTIPASS OPTICAL RETROREFLECTOR AND METHOD OF USING

(75) Inventor: Marc Currie, Arlington, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 199 days.

(21) Appl. No.: 10/165,913

(22) Filed: Jun. 11, 2002

(65) Prior Publication Data
US 2003/0227681 A1 Dec. 11, 2003

(51) Int. Cl.[7] ............................................. G02B 5/122
(52) U.S. Cl. ...................................... 359/529; 359/834
(58) Field of Search ................................. 359/529, 831, 359/834, 222, 857; 385/18

(56) References Cited

U.S. PATENT DOCUMENTS

| | | |
|---|---|---|
| 3,437,954 A | 4/1969 | Herriott et al. |
| 5,291,265 A | 3/1994 | Kebabian |
| 5,973,864 A | 10/1999 | Lehmann et al. |
| 6,198,574 B1 * | 3/2001 | Hill ............................. 359/497 |
| 6,275,626 B1 * | 8/2001 | Laor ............................ 385/18 |

OTHER PUBLICATIONS

Herriott et al., Folded Optical Delay Lines, Aug. 1965, vol. 4, No. 8, Applied Optics,pp. 883-889.

* cited by examiner

*Primary Examiner*—James Phan
(74) *Attorney, Agent, or Firm*—John J. Karasek; George A. Kap

(57) ABSTRACT

This invention pertains to a multipass retroreflector and to a method for its operation. In a preferred embodiment, the retroreflector comprises three reflecting surfaces arranged at an angle to each other in the form of a prism that is triangular in cross-section and 1 to 2 ports through which an optical beam enters and/or exits. The method includes the step of admitting an optical beam into the retroreflector where the optical beam is reflected from the reflecting surfaces and exits parallel to the path of the incoming optical beam. The method also includes the steps of spacing and adjusting angular disposition and dimensions of the reflecting surfaces in order to change path length of the optical beam passing through the retroreflector. This spacing can be continuously scanned causing a large change in optical path length due to a small change in the position of the moving surface.

14 Claims, 2 Drawing Sheets

MULTIPASS OPTICAL RETROREFLECTOR AND METHOD OF USING

BACKGROUND OF THE INVENTION

1. Field of the Invention

This invention pertains to the field of collinear and non-collinear retroreflectors and to methods for their operation.

2. Description of Related Art

Multipass optical cells have been used for many years in the field of gas and atmospheric absorption spectroscopy so that a small volume can be interrogated by making multiple passes through the volume. This achieves a long optical path length in a very compact structure, or similarly, amplifies via multiple passes a weak optical response of a single pass.

Retroreflection of an optical signal is very important in optical systems since it not only reflects the light, but also causes the return optical path to be parallel to the incident path. This has many applications such as optical delay line scanning, optical alignment, and bright passive reflections such as road signs, to name a few.

Combining the trait of a multipass optical cell with a retroreflector creates a flexible tool for use in compact laser amplifier gain stages, communication, spectroscopy, and remote sensing.

Donald R. Herriott and Harry J. Schulte in an article entitled "Folded Optical Delay Lines" in the journal *Applied Optics*, for August 1965, vol. 4, No. 8, starting on p. 883, disclose that a long optical path has been folded between two 7.5 cm diameter spherical or aspherical mirrors to provide an output optical beam which can be well separated from previous reflections with 1000 or more passes between the mirrors. The 3000-m path provides 10 μsec of delay. This system can be used as a dispersionless optical delay line for use in filtering or storage of information modulated onto the light beam. The pattern of beams between the two mirrors is obtained in one of two ways. A small perturbing mirror may be inserted to give a series of offset ellipses, or one or both of the mirrors can be made astigmatic to give a Lissajous pattern of spots on each mirror. The output beam can be separated from others by discriminating in both angle and position. The diffraction losses of the system are much lower than those for an open beam because of the periodic focusing of the spherical mirrors. The extreme dependence of the loss of the delay line upon the absorption and scattering loss of the mirrors makes the system a suitable method for measuring mirror loss.

U.S. Pat. No. 5,973,864 to Lehman et al discloses a stable resonator for a ring-down cavity spectroscopy cell having an optic axis. The resonator includes two Brewster's angle retroreflector prisms, each having a plurality of total internal reflection surfaces. The prisms are disposed in alignment along the optic axis of the resonator. One or both of the prisms can be rotated so that light rays enter a surface of the prism nearly at Brewster's angle to the normal of the prism surface. This feature maintains alignment between the prisms and allows the resonator to be tuned. One of the internal reflection surfaces of at least one of the prisms may be a curved surface. Alternatively, an astigmatic lens may be centered in one arm of the resonator and tilted at Brewster's angle with respect to the optic axis of the resonator.

OBJECTS AND BRIEF SUMMARY OF THE INVENTION

An object of this invention is a collinear or non-collinear optical retroreflector and method of operating or using same.

Another object of this invention is a simple and compact design for a multipass optical cell.

Another object of this invention is a device that can be used as a stand-alone multipass optical retroreflector or as a scanning optical delay line.

Another object of this invention is an optical delay line device that can achieve large delays with small structural displacements therein.

Another object of this invention is an optical retroreflector that is scalable.

These and other objects of this invention can be achieved by a device that includes three or more cooperating reflective surfaces or mirrors and at least one non-reflective port that allows light to enter and/or exit after reflections from the reflective surfaces.

DETAILED DESCRIPTION OF THE INVENTION

This invention combines the concepts of optical beam retroreflection and optical multipass cells. The invention discloses a retroreflecting optical geometry that reflects the incident optical beam from the reflecting surfaces back upon the identical incident path or another path that is parallel to the incident path. Within the boundaries of this cell or device, the optical beam undergoes multiple reflections. The number of reflections within the cell is a function of the boundary angles, dimensions of the reflecting surfaces and the position of the incident optical beam.

This invention describes a novel design to achieve a multipass optical cavity that is naturally retroreflecting upon the exact path of the incident light or another path that is parallel thereto. This is achieved by placing, typically, three reflective surfaces in a prism-like geometry, while allowing a non-reflective break(s) or port(s) in one surface to allow the light to enter and exit. In one embodiment, the retroreflection is collinear, thereby causing the optical beam to enter and exit the retrorelector from the same port whereas in another embodiment, the retroreflection is non-collinear where the light or optical beam enters and exits the retroreflector through different ports.

Figure 1:
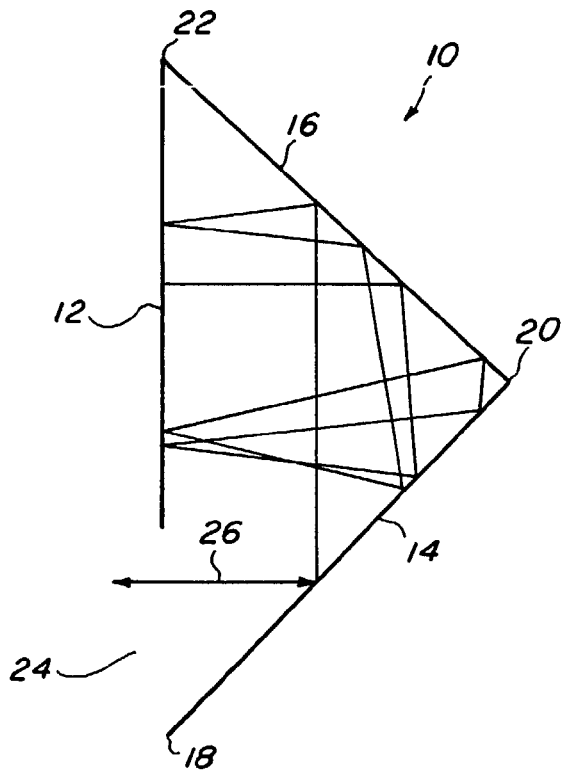
FIG. 1 is a cross-sectional view of an optical device or a collinear retroreflector.

The concept of this invention is shown in FIG. 1 where a collinear retroreflector in the form of a structure or prism 10 is composed of internally reflecting surfaces 12, 14, 16, which are not transparent to a light beam. The reflecting surfaces are disposed at an angle to each other and, typically, abut and are fixed to each other at corners 18, 20, 22 to form the triangular structure in cross-section except that at corner 18, there is a port or a gap 24 which forms an inlet through which a light beam from a light source enters the interior of the structure. As will be later explained, more than one port in the structure can be provided, typically at an edge of one of the reflecting surfaces. Furthermore, the port can be a continuation of surface 12 where a portion of the surface is transparent to light.

Continuation of surface 12 can extend to where it abuts and is fixed to surface 14.

The reflective surfaces can be coated with optical modulators for modulation of the incident optical beam or thin-film materials for analysis and/or evaluation.

It should be understood that surfaces 12, 14, 16, here and in other embodiments, need not be affixed to each other in this or other embodiments of this invention, but can be loosely arranged and held in place by outside means so that the desired reflections are obtained through adjustments of the reflecting surfaces relative to each other or otherwise. For some spectroscopic applications, the surfaces must form a fully enclosed, hermetic prism so that a fluid can be held therein and analyzed by passing an optical beam therethrough.

A collinear retroreflector has one port where the inlet optical beam enters and the exit optical beam exits, after reflecting off the reflecting surfaces, along the same path as the inlet optical beam. The port can be positioned anywhere, however, but it is typically positioned along an edge of the surface 12.

A collinear retroreflector shown in FIG. 1 and having angle at corner 18 of 45°, angle at corner 20 of 87°, and angle at corner 22 of 48°, contains 23 reflections. If reflectivity of the reflective surfaces 12, 14, 16 is 99%, optical losses due to reflectivity of 99%, is 21%.

The vertical reflecting surface or mirror 12 has port 24 at the bottom, but this port can be at the top or an aperture or opening can be created in the center or anywhere else in the reflecting surface. Operation of or method of using the collinear retroreflector 10 of FIG. 1 involves passing an optical beam along path 26 into retroreflector 10 whereby the optical beam is reflected numerous times from the reflecting surfaces 12, 14, 16 and then exits the retroreflector 10 along path 26. Source of the optical beam can be anything available, including a light bulb or a laser. The method also allows for the continuous changing of optical path length, and thus of optical time delay, by moving or scanning one of the surfaces. The method also includes multiple reflections and the movement of one surface to cause a large change in optical path length through a small change in the position of the moving surface, thereby creating large changes in optical time delay.

Figure 2:
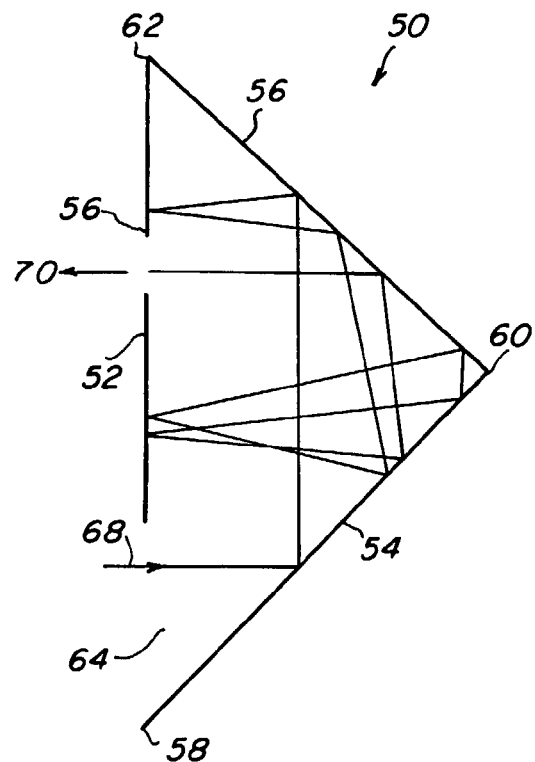
FIG. 2 is a cross-sectional view of an optical device or a non-collinear retroreflector.

FIG. 2 shows a non-collinear retroreflector 50 composed of internally reflecting surfaces 52, 54, 56 which are not transparent to an optical beam. The reflecting surfaces are disposed at an angle to each other and, typically, abut and are affixed to each other at corners 58, 60, 62 and along the edges of the reflecting surfaces except for the presence of two ports 64, 66 through which an optical beam enters and exits from interior of the retoreflector. The reflecting surfaces form a structure that is triangular in cross-section. A non-collinear retoreflector is characterized by the fact that the optical beam enters along one path but leaves the retoreflector by another parallel path. Ports 64, 66 can be a continuation of surface 52 but the surface must be transparent to the optical beam at ports 64, 66.

Operation of the non-collinear retroreflector 50 of FIG. 2 involves passing an optical beam (light) along path 68 through port 64 into retroreflector 50 wherein the optical beam is reflected from the interiorly reflecting surfaces 52, 54, 56 and then exits through port 66 along path 70, which is parallel to path 68.

Figure 3:
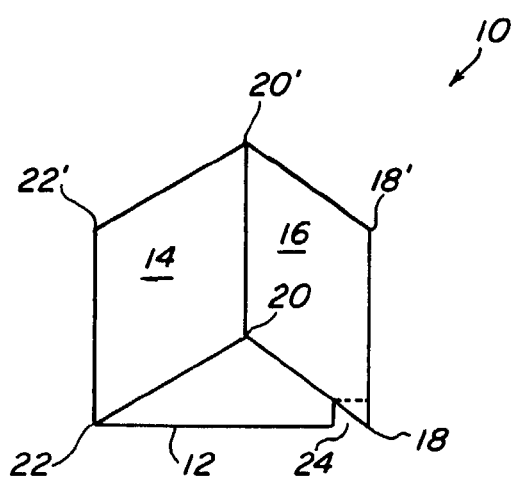
FIG. 3 is an isometric view of the retroreflector of FIG. 1.

FIG. 3 is an isometric view of the retroreflector of FIG. 1 showing the retroreflector in the form of a prism that is triangular in cross-section. The retroreflector 10 comprises internally reflecting surfaces 12, 14, 16 which form a prism with acute angle at corner 20 and acute angles at corners 18, 22. Port 24 is adjacent to corner 18 but can be anywhere in the reflecting surface 12. The port can be in the form of a slit which extends the length of surface 12 but it is typically in the form an opening of sufficient size to allow passage of an optical beam. Surfaces 12, 14, 16 are typically rectangular but can be of any other shape, planar or curved, depending on design of the retroreflector. It should be understood that rectangular figures include squares. Surface 12 in FIG. 3 is shown as a line, however, it should be understood that it is rectangular with its edge extending the width between reference numbers 18 and 22 and in depth between reference numbers 22 and 22' or 18 and 18', except for port 24 which can be a slit extending the depth of surface 12 or a corner opening. Reference numerals 18', 20', and 22' denote the depth extent of the reflective surfaces starting at corners 18, 20 , 22, respectively. Although three reflecting surfaces are shown for retroreflector 10, it should be understood that any number in excess of three reflecting surfaces can be used to construct a retroreflector to have an optical beam reflect from the reflecting surfaces for spectroscopic purposes or for increasing path length of an optical beam in order to obtain the desired time delay for communications or any other application.

Figure 4:
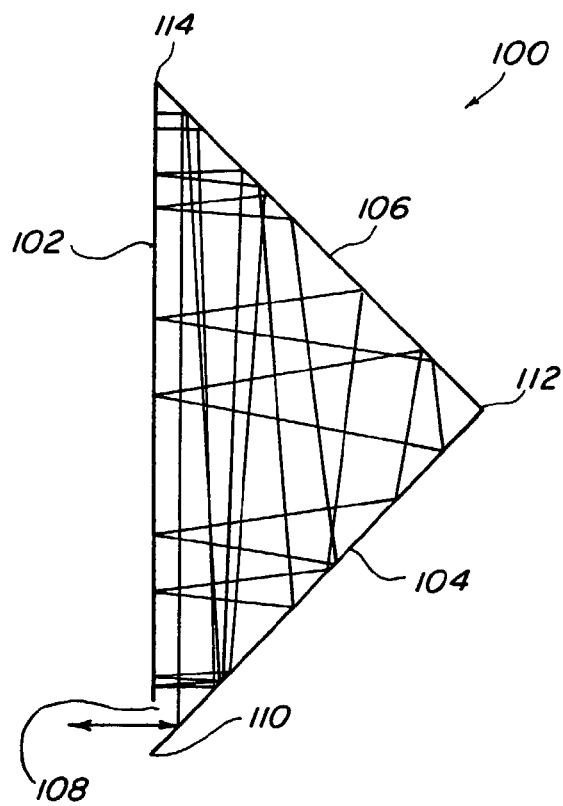
FIG. 4 is a cross-sectional view of another collinear rotoreflector having a path length of an optical beam that is longer than that of the retroreflector of FIG. 1.

To increase the number of passes of the optical beam, the angles are adjusted to increase the path length. FIG. 4 illustrates a collinear retroreflector 100 consisting of reflecting surfaces or mirrors 102, 104, 106. Surface 102 is vertically disposed, lower surface 104 is disposed upwardly at an acute angle to the vertical, and the upper surface 106 is disposed downwardly at an acute angle from the vertical. Retroreflector 100 shown in FIG. 4 includes port 108 which can be a slit extending the extent of surface 102 but is typically a corner opening. Vertical surface 102 meets lower surface 104 at corner 110, in absence of port 108, and upper surface 106 meets the vertical reflecting surface 102 at corner 114. Upper surface 106 and lower surface 104 meet at corner 112. As shown in FIG. 4, the reflecting surfaces form retroreflector 100 with an interior volume wherein an optical beam is reflected many times before exiting. Number of reflections for the retroreflector 100 is 59 if the corner angle from the vertical at corner 110 is 45°; angle at corner 112 is 89°; angle at corner 114 is 46°.

For comparison, a particular embodiment of FIG. 1 has angles of 45°, 48°, and 87° at corners 18, 22 and 20, respectively, and a particular embodiment of FIG. 4 is similar since the angle at corner 110 is 45°, similar to that of corner 18 in FIG. 1, but the angle at corner 112 has increased to 89° from its corresponding 87° angle at corner 20 in FIG. 1. This changes corner 116 in FIG. 4 to 46° from its corresponding 48° angle at corner 22 in FIG. 1. Implementing these changes increases the optical path length in the FIG. 4 embodiment by 145% over that in FIG. 1.

Figure 5:
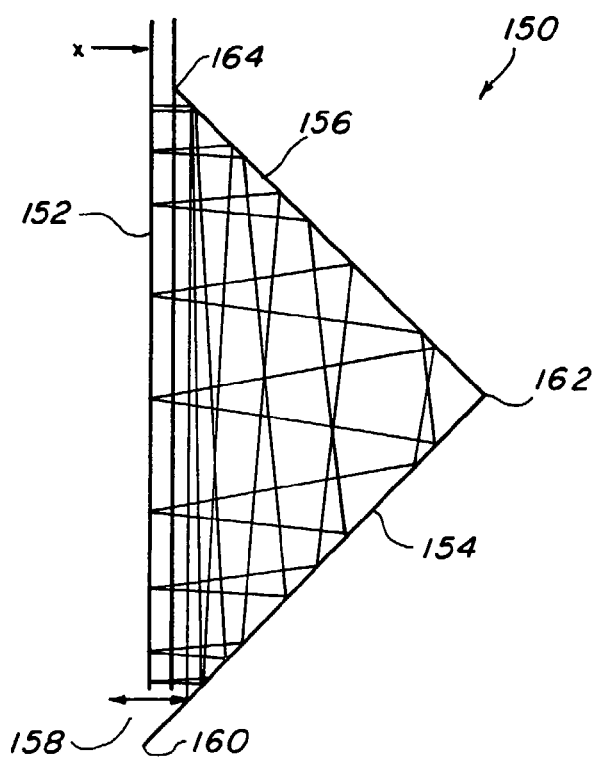
FIG. 5 is a cross-sectional view of a collinear retroreflector wherein optical delay line scanning causes small movement of a single reflecting surface to be magnified creating a large change in optical delay.

FIG. 5 illustrates a collinear retroreflector 150 which is composed of reflecting surfaces 152, 154, 156 and port 158, similar to the retroreflector 100 of FIG. 4. Corner 160 is at bottom of the retroreflector 150 shown in FIG. 5, corner 162 is up and to the right of corner 160, and corner 164 is above corner 160. Retroreflector 150 of FIG. 5 is the same as the retroreflector 100 of FIG. 4 with one exception: surface 152 is scanned or displaced from the rest of the retroreflector by a distance X in order to create an optical time delay caused by a small movement of the reflective surface which is magnified yielding a large change in optical delay. Displacement X is offset a uniform distance from the retroreflector although it is typically scanned or continuously moved over the distance X. Although reflecting surface 152 is spaced from the rest of the retrorefletor, the surfaces form a space, although the space may be hermetically enclosed using a fixed transparent surface to the right of surface 152.

The device disclosed herein, i.e., a multiple pass retroreflector, is useful for optical delay scanning since movement of a single reflective surface or mirror is magnified by the multiple reflections off its surface creating a large change in optical delay for a small change in mirror position. For instance, if the vertical surface 102 is 100 units in length, moving it 5 units to the left where X is 5 units, produces a 199 unit change in path length. Thus, in an optical micro-electro mechanical system, or MEMS, with a 1-mm mirrored surface, a 50-$\mu$m scan of the mirror to the left (X=50 $\mu$m), produces a 1.99 mm increase in optical path length, which is equivalent to 6.6 ps time delay in free space.

The figures show the incident optical beam arriving at a 90-degree angle to the vertical mirror. In actuality, there are several incident angles that contain solutions for retroreflection.

Reflectivity of the reflecting surfaces is below 100% and it is typically 99% and higher, such as 99.99%. The reflective surfaces are typically made from fused silica, sapphire or diamond, or any other suitable material, and for MEMs applications silicon can be used. Dielectric coatings on the surface of these materials can be used to increase their reflectivity to greater than 99.99%.

The device disclosed herein is scalable, due to its small number of components, in a simple geometrical arrangement making it useful in microoptics, monolithic integration, optical MEMs, macroscopic scale optical components, and it can be fabricated on a wide variety of materials.

The device can be made from a single material polished and/or coated for increased reflectivity. The device can also be made from an optically amplifying medium, as in block form, to amplify the light as it passes from the port of entry to the port of exit of the device.

While presently preferred embodiments have been shown of the novel retroreflector and method for its operation or use, and several modifications discussed, persons skilled in this art will readily appreciate that various additional changes and modifications can be made without departing from the spirit of the invention as defined and differeniated by the following claims.

What is claimed is:

1. A method of using a multipass retroreflector made of at least three reflecting surfaces arranged at non-90° angles to each other and at least one port whereby an optical beam can enter and/or exit the retroreflector through at least one of the ports, the method comprising the step of passing an inlet optical beam into the retroreflector through one of the ports whereby the optical beam is reflected from each reflecting surface multiple times and exits the retroreflector along a path that is parallel to the path of the inlet optical beam.

2. The method of claim 1 wherein the retroreflector comprises three reflective surfaces arranged at an angle to each other and 1 to 2 ports for allowing optical beam to enter and/or exit the retroreflector, the reflecting surfaces forming a prism that is triangular in cross-section, the method further includes the step of adjusting at least one angle between the reflecting surfaces in order to change path length of the optical beam reflected from the reflecting surfaces.

3. The method of claim 2 including step of displacing at least one of the reflecting surfaces in order to change path length of the optical beam reflected from the reflecting surfaces.

4. The method of claim 1 including the step of hermetically sealing space formed by the reflecting surfaces for enclosing a fluid in the retroreflector for spectroscopic testing.

5. The method of claim 1 wherein the retroreflector comprises three reflecting surfaces and two ports, the method further includes the step of allowing the optical beam reflected from the reflecting surfaces to exit through a port other than the port of entry, reflectivity of the reflecting surfaces is at least 99% and the reflecting surfaces are made from a material selected from the group consisting of silica, sapphire, diamond and mixtures thereof and mixtures containing at least one of these materials.

6. The method of claim 1 wherein the retroreflector comprises three reflecting surfaces and one port, the method further including the step of allowing the optical beam reflected from the reflecting surfaces to exit, through the same port through which the optical beam entered the retroreflector, reflectivity of the reflecting surfaces is at least 99% and the reflecting surfaces are made from a material selected from the group consisting of silica, sapphire, diamond and mixtures thereof and mixtures containing at least one of these materials.

7. The method of claim 1 including the step of continuously moving at least one of the reflecting surfaces toward or away from the retroreflector in order to continuously change the optical path of the optical beam entering the retroreflector.

8. A multipass retroreflector device comprising three rectangular reflecting surfaces arranged at non-90° angles to each other and 2 openings disposed in one of said reflecting surfaces whereby an input optical beam enters said device through one of said two openings and reflected from the reflecting surfaces before exiting said device as an output beam through the other of said two openings along a path that is parallel to the path of the input optical beam, wherein said three rectangular surfaces form a structure that is triangular in cross-section.

9. The multipass retroreflector device of claim 8 wherein two openings are disposed along one edge of one of said reflecting surfaces.

10. A multipass retroreflector device comprising three internally rectangular reflecting surfaces arranged at non-90° angles to each other forming a triangular structure in cross-section enclosing space and a port for inlet and outlet optical beam, wherein said port is disposed at a corner of one of said reflecting surfaces.

11. The multipass retroreflector device of claim 10 wherein at least one of said reflecting surfaces is spaced from said retroreflector in order to change path length of an optical beam reflected said reflecting surfaces.

12. The multipass retroreflector device of claim 11 wherein said reflecting surfaces have reflectivity of at least 99% and are made of fused silica.

13. The multipass retroreflector device of claim 11 wherein said reflecting surfaces are made from a material selected from the group consisting of fused silica, sapphire, diamond and mixtures containing at least one of the material.

14. A multipass retroreflector device comprising three internally reflecting surfaces arranged at non-90° angles to each other forming a triangular structure in cross-section enclosing space and 2 ports for inlet and outlet optical beam; said retroreflector device is made in block form formed from a single material, wherein said reflecting surfaces comprise sides of said block and said ports are enhanced surfaces which are less reflective than said reflecting surfaces, and wherein said material is optically amplifying that can amplify light entering said retroreflector through one of said ports.

* * * * *